United States Patent [19]

Cook et al.

[11] Patent Number: 5,541,307
[45] Date of Patent: Jul. 30, 1996

[54] BACKBONE MODIFIED OLIGONUCLEOTIDE ANALOGS AND SOLID PHASE SYNTHESIS THEREOF

[75] Inventors: Phillip D. Cook, Carlsbad; Yogesh S. Sanghvi, San Marcos, both of Calif.; Francois Morvan, Montpellier, France

[73] Assignee: ISIS Pharmaceuticals, Inc., Carlsbad, Calif.

[21] Appl. No.: 174,379

[22] Filed: Dec. 28, 1993

Related U.S. Application Data

[63] Continuation-in-part of Ser. No. 40,903, filed as PCT/US92/04294, May 21, 1992, Pat. No. 5,386,023, which is a continuation-in-part of Ser. No. 903,160, Jun. 24, 1992, abandoned, which is a continuation-in-part of Ser. No. 703,619, May 21, 1991, Pat. No. 5,378,825, which is a continuation-in-part of Ser. No. 566,836, Aug. 13, 1990, Pat. No. 5,223,618, and Ser. No. 558,663, Jul. 27, 1990, Pat. No. 5,138,045.

[51] Int. Cl.$^6$ .............................. C07H 1/00; C07H 19/00; C07H 21/00
[52] U.S. Cl. ................... 536/23.1; 536/25.3; 536/25.32; 536/25.33; 536/25.34; 536/25.6
[58] Field of Search .................................. 536/23.1, 25.3, 536/25.32, 25.34, 26.7, 26.8

[56] References Cited

U.S. PATENT DOCUMENTS

| | | | |
|---|---|---|---|
| 3,687,808 | 8/1972 | Merigan, Jr. et al. | 195/28 |
| 4,707,440 | 11/1987 | Stavrianopoulos | 536/25.3 |
| 5,138,045 | 8/1992 | Cook et al. | 536/24.5 |
| 5,223,618 | 6/1993 | Cook et al. | 544/276 |
| 5,378,825 | 1/1995 | Cook et al. | 536/25.34 |
| 5,386,023 | 1/1995 | Sanghvi et al. | 536/25.3 |

OTHER PUBLICATIONS

Alul et al., "Oxalyl–CPG: a labile support for synthesis of sensitive oligonucleotide derivatives," *Nucleic Acids Research*, 19:1527–1532, 1991.

Balgobin et al., "Solid Phase Synthesis of DNA Under a Non–Depurinative Condition With a Base Labile 5'–Protecting Group (Fmoc) using Phosphiteamidite Approach," *Nucleosides and Nucleotides*, 6:461–463, 1987.

Beaucage et al., "Advances in the Synthesis of Oligonucleotides by the Phosphoramidite Approach," *Tetrahedron*, 48:2223–2311, 1992.

Bellon et al., "4'–Thio–oligo–β–D–ribonucleotides: synthesis of β–4'–thio–oligouridylates, nuclease resistance, base pairing properties, and interaction with HIV–1 reverse transcriptase," *Nucleic Acids Res.*, 21:1587–1593, 1993.

Cormier et al., "Synthesis of hexanucleotide analogues containing diisopropylsilyl internucleotide linkages," *Nucleic Acids Research*, 16:4583–4594, 1988.

Damha et al., "An improved procedure for derivatization of controlled–pore glass beads for solid–phase oligonucleotide synthesis," *Nucleic Acids Research*, 18:3813–3821, 1990.

Jones, R.A., "Preparation of Protected Deoxyribonucleosides," *Oligonucleotide Synthesis*, Gait, ed., Oxford: IRL Press, Chapter 2, 1984.

Li et al., "Synthesis and Characterization of Oligonucleotides Containing 4–O–Methylthymine," *Biochemistry*, 26:1086–1093, 1987.

Loke et al., "Delivery of c–myc Antisense Phosphorothioate Oligodeoxynucleotides to Hematopoietic Cells in Culture by Liposome Fusion: Specific Reduction in c–myc Protein Expression Correlates with Inhibition of Cell Growth and DNA Synthesis," *Top. Microbiol. Immunol.*, 141:282–289, 1988.

Ma et al., "The 9–Fluorenylmethyloxycarbonyl Group as a 5'–OH Protection in Oligonucleotide Synthesis," *Biopolymers*, 28:965–993, 1989.

Marcus–Sekura et al., "Comparative inhibition of chloramphenicol acetyltransferase gene expression by antisense oligonucleotide analogues having alkyl phosphotriester, methylphosphonate and phosphorothioate linkages," *Nucleic Acids Research*, 15:5749–5763, 1987.

Matteucci, "Deoxyoligonucleotide Analogs Based on Formacetal Linkages," *Tetrahedron Letters*, 31:2385–2388, 1990.

Mazur et al., "Isosteres of Natural Phosphates. 11. Synthesis of a Phosphonic Acid Analogue of an Oligonucleotide," *Tetrahedron*, 40:3949–3956, 1984.

Miller et al., "Effects of a Trinucleotide Ethyl Phosphotriester, G$^m$p (Et)G$^m$p(Et)U, on Mammalian Cells in Culture," *Biochemistry*, 16:1988–1996, 1977.

Nair, "Regiospecific 5'–Silylation of Nucleosides," *Org. Prep. Proc. Int.*, 22:57–61, 1990.

Robins et al., "Nucleic Acid Related Compounds. 42. A General Procedure for the Efficient Deoxygenation of Secondary Alcohols. Regiospecific and Stereoselective Conversation of Ribonucleosides to 2'–Deoxynucleosides," *J. Am. Chem. Soc.*, 105:4059–4065, 1983.

Stirchak et al., "Uncharged Stereoregular Nucleic Acid Analogues. 1. Synthesis of a Cytosine–Containing Oligomer with Carbamate Internucleoside Linkages," *J. of Organic Chemistry*, 52:4202–4206, 1987.

Wilson, "Cellular Transport Mechanisms," *Ann. Rev. Biochem.*, 47:933–965, 1978.

Wright et al., "Large Scale Synthesis of Oligonucleotides via Phosphoramidite Nucleosides and a High–loaded Polystyrene Support," *Tetrahedron Letters*, 34:3373–3376, 1993.

Coull et al., Tetrahedron Letters, vol. 28, No. 7, pp. 745–748, (1987).

Goodchild, Bioconjugate Chemistry, vol. 1, No. 3, pp. 165–187, (1990).

Stirchak et al., J. Org. Chem. vol. 52, pp. 4202–4206, (1987).

*Primary Examiner*—Douglas W. Robinson
*Assistant Examiner*—James O. Wilson
*Attorney, Agent, or Firm*—Woodcock Washburn Kurtz Mackiewicz & Norris

[57] ABSTRACT

Compounds and methods for preparing oligonucleotide analogs are provided. In preferred embodiments, the methods involve solid-phase coupling of synthons bearing either 3'-electrophillic groups and 5'-nucleophilic groups or 5'-electrophillic groups and 3'-nucleophilic groups to form neutral, achiral oligomers.

32 Claims, 3 Drawing Sheets

0716-01.CHM
1
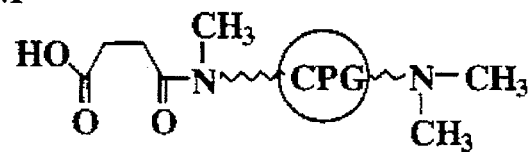
2
CPG = Controlled Pore Glass
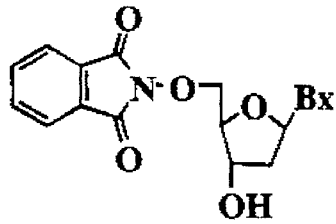
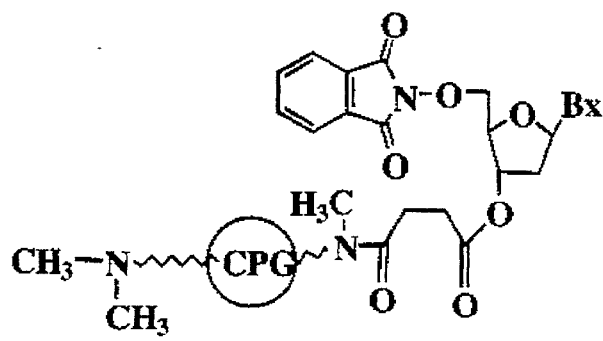
3 Bx = thymine
4 Bx = adenine
5 Bx = N-2-isobutyryl-O-6-
   diphenylcarbamoyl-
   guanine
6 Bx = N-4-protected-cytosine
7 Bx = N-4-protected-5-methyl-
   cytosine
8 Bx = thymine
9 Bx = adenine
10 Bx = N-2-isobutyryl-O-6-
   diphenylcarbamoyl-
   guanine
11 Bx = N-4-protected-cytosine
12 Bx = N-4-protected-5-methyl-
   cytosine
FIG. 1

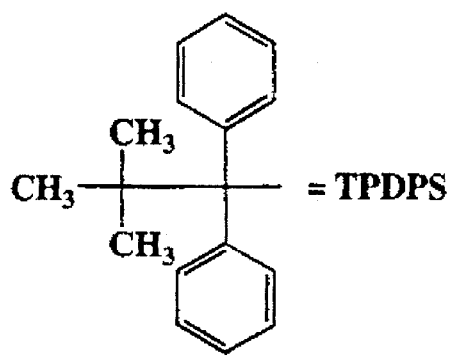 = TPDPS

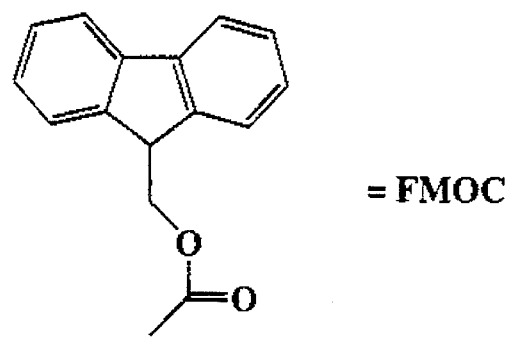 = FMOC

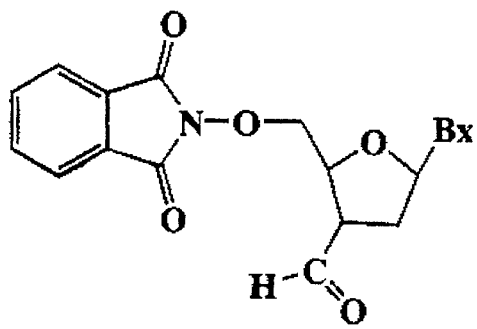

13 Bx = thymine
14 Bx = adenine
15 Bx = N-2-isobutyryl-guanine
16 Bx = N-4-protected-cytosine
17 Bx = N-4-protected-5-
    methyl-cytosine

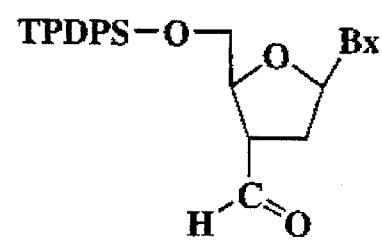

18 Bx = thymine
19 Bx = adenine
20 Bx = N-2-isobutyryl-guanine
21 Bx = N-4-protected-cytosine
22 Bx = N-4-protected-5-
    methyl-cytosine

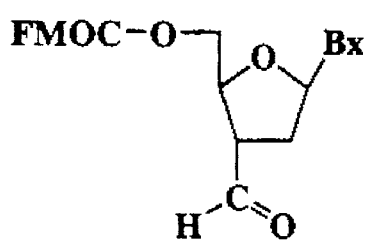

23 Bx = thymine
24 Bx = adenine
25 Bx = N-2-isobutyryl-guanine
26 Bx = N-4-protected-cytosine
27 Bx = N-4-protected-5-methyl-
    cytosine

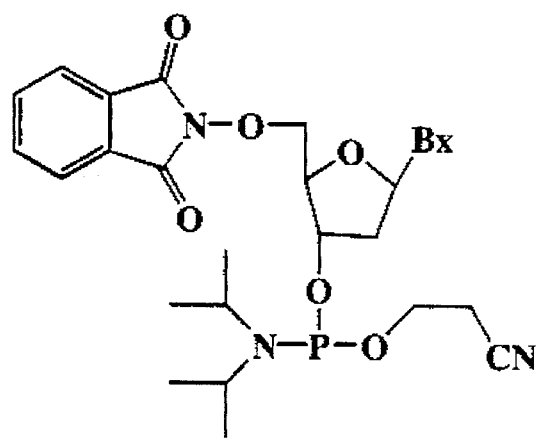

28 Bx = thymine
29 Bx = adenine
30 Bx = N-2-isobutyryl-guanine
31 Bx = N-4-protected-cytosine
32 Bx = N-4-protected-5-methyl-
    cytosine

FIG. 2

BACKBONE MODIFIED OLIGONUCLEOTIDE ANALOGS AND SOLID PHASE SYNTHESIS THEREOF

CROSS REFERENCE TO RELATED APPLICATIONS

This application is a continuation-in-part of U.S. Ser. No. 08/040,903, filed Mar. 31, 1993, now U.S. Pat. No. 5,386,023, which is a continuation-in-part of PCT/US92/04294, filed May 21, 1992, and of U.S. Ser. No. 903,160, filed Jun. 24, 1992, now abandoned which are continuations-in-part of U.S. Ser. No. 703,619, filed May 21, 1991, now U.S. Pat. No. 5,378,825, which is a continuation-in-part of U.S. Ser. No. 566,836 filed on Aug. 13, 1990, and U.S. Ser. No. 558,663 filed on July 27, 1990, now U.S. Pat. No. 5,138,045. This application also is related to the subject matter disclosed and claimed in the following patent applications filed herewith by the present inventors: U.S. Ser. No. 08/39,979, filed Mar. 30, 1993, now abandoned; U.S. Ser. No. 08/40,526, filed Mar. 31, 1993, now U.S. Pat. No. 5,323,613; and U.S. Ser. No. 08/40,933, filed Mar. 31, 1993, now abandoned. Each of these patent applications are assigned to the assignee of this application and are incorporated by reference herein.

FIELD OF THE INVENTION

This invention relates to the synthesis of nuclease resistant oligonucleotide analogs which are useful for therapeutics, diagnostics and as research reagents. In particular, the invention relates to solid-phase synthetic methods wherein amine-terminated synthons are coupled with aldehyde-terminated synthons to produce hydroxylaminoc-ontaining and/or hydrazino-containing covalent linkages.

BACKGROUND OF THE INVENTION

It is well known that most of the bodily states in mammals, including most disease states, are effected by proteins. Proteins, either acting directly or through their enzymatic functions, contribute in major proportion to many diseases in animals and man.

Classical therapeutics-generally has focused upon interactions with proteins in an effort to moderate their disease causing or disease potentiating functions. Recently, however, attempts have been made to moderate the production of proteins by interactions with the molecules (i.e., intracellular RNA) that direct their synthesis. These interactions have involved hybridization of complementary "antisense" oligonucleotides or certain analogs thereof to RNA. Hybridization is the sequence-specific hydrogen bonding of oligonucleotides or oligonucleotide analogs to RNA or to single stranded DNA. By interfering with the production of proteins, it has been hoped to effect therapeutic results with maximum effect and minimal side effects.

The pharmacological activity of antisense oligonucleotides and oligonucleotide analogs, like other therapeutics, depends on a number of factors that influence the effective concentration of these agents at specific intracellular targets. One important factor for oligonucleotides is the stability of the species in the presence of nucleases. It is unlikely that unmodified oligonucleotides will be useful therapeutic agents because they are rapidly degraded by nucleases. Modification of oligonucleotides to render them resistant to nucleases therefore is greatly desired.

Modification of oligonucleotides to enhance nuclease resistance generally has taken place on the phosphorus atom of the sugar-phosphate backbone. Phosphorothioates, methyl phosphonates, phosphoramidates and phosphorotriesters have been reported to confer various levels of nuclease resistance. Phosphate-modified oligonucleotides, however, generally have suffered from inferior hybridization properties. See, e.g., Cohen, J. S., ed. *Oligonucleotides: Antisense Inhibitors of Gene Expression*, (CRC Press, Inc., Boca Raton Fla., 1989).

Another key factor is the ability of antisense compounds to traverse the plasma membrane of specific cells involved in the disease process. Cellular membranes consist of lipid-protein bilayers that are freely permeable to small, nonionic, lipophilic compounds and are inherently impermeable to most natural metabolites and therapeutic agents. See, e.g., Wilson, *Ann. Rev. Biochem.* 1978, 47, 933. The biological and antiviral effects of natural and modified oligonucleotides in cultured mammalian cells have been well documented. It appears that these agents can penetrate membranes to reach their intracellular targets. Uptake of antisense compounds into a variety of mammalian cells, including HL-60, Syrian Hamster fibroblast, U937, L929, CV-1 and ATH8 cells has been studied using natural oligonucleotides and certain nuclease resistant analogs, such as alkyl triesters and methyl phosphonates. See, e.g., Miller, etal., *Biochemistry* 1977, 16, 1988; Marcus-Sekura, etal., *Nucleic Acids Research* 1987, 15, 5749; and Loke, et al., *Top. Microbiol. Immunol.* 1988, 141, 282.

Often, modified oligonucleotides and oligonucleotide analogs are internalized less readily than their natural counterparts. As a result, the activity of many previously available antisense oligonucleotides has not been sufficient for practical therapeutic, research or diagnostic purposes. Two other serious deficiencies of prior art compounds designed for antisense therapeutics are inferior hybridization to intracellular RNA and the lack of a defined chemical or enzyme-mediated event to terminate essential RNA functions.

Modifications to enhance the effectiveness of the antisense oligonucleotides and overcome these problems have taken many forms. These modifications include base ring modifications, sugar moiety modifications and sugar-phosphate backbone modifications. Prior sugar-phosphate backbone modifications, particularly on the phosphorus atom, have effected various levels of resistance to nucleases. However, while the ability of an antisense oligonucleotide to bind to specific DNA or RNA with fidelity is fundamental to antisense methodology, modified phosphorus oligonucleotides have generally suffered from inferior hybridization properties.

Replacement of the phosphorus atom has been an alternative approach in attempting to avoid the problems associated with modification on the pro-chiral phosphate moiety. For example, Matteucci, *Tetrahedron Letters* 1990, 31, 2385 disclosed the replacement of the phosphorus atom with a methylene group. However, this replacement yielded unstable compounds with nonuniform insertion of formacetal linkages throughout their backbones. Cormier, et al., *Nucleic Acids Research* 1988, 16, 4583, disclosed replacement of phosphorus with a diisopropylsilyl moiety to yield homopolymers having poor solubility and hybridization properties. Stirchak, et al., *Journal of Organic Chemistry* 1987, 52, 4202 disclosed replacement of phosphorus linkages by short homopolymers containing carbamate or morpholino linkages to yield compounds having poor solubility and hybridization properties. Mazur, et al., *Tetrahedron* 1984, 40, 3949, disclosed replacement of a phosphorus

3 linkage with a phosphonic linkage yielded only a homotrimer molecule. Goodchild, *Bioconjugate Chemistry* 1990, 1, 165, disclosed ester linkages that are enzymatically degraded by esterases and, therefore, are not suitable for antisense applications.

The limitations of available methods for modification of the phosphorus backbone have led to a continuing and long felt need for other modifications which provide resistance to nucleases and satisfactory hybridization properties for antisense oligonucleotide diagnostics and therapeutics.

OBJECTS OF THE INVENTION

It is an object of the invention to provide oligonucleotide analogs for diagnostic, research, and therapeutic use.

It is a further object of the invention to provide oligonucleotide analogs capable of forming duplex or triplex structures.

It is a further object of the invention to provide oligonucleotide analogs having enhanced cellular uptake.

Another object of the invention is to provide oligonucleotide analogs having greater efficacy than unmodified antisense oligonucleotides.

It is yet another object of the invention to provide methods for synthesis and use of oligonucleotide analogs.

These and other objects will become apparent to persons of ordinary skill in the art from a review of the present specification and the appended claims.

SUMMARY OF THE INVENTION

The present invention provides novel compounds that mimic and/or modulate the activity of wild-type nucleic acids. In general, the compounds contain a selected nucleoside sequence which is specifically hybridizable with a targeted nucleoside sequence of single stranded or double stranded DNA or RNA. At least a portion of the compounds of the invention has structure I:

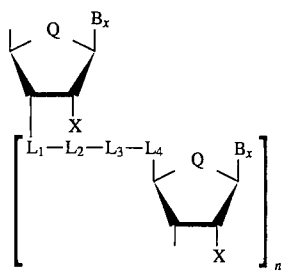

wherein:

$L_1$—$L_2$—$L_3$—$L_4$ is $CH_2$—$R_A$—$NR_1$—$CH_2$, $CH_2$—$NR_1$—$R_A$—$CH_2$, $R_A$—$NR_1$—$CH_2$—$CH_2$, $CH_2$—$CH_2$—$NR_1$—$R_A$, $CH_2$—$CH_2$—$R_A$—$NR_1$, or $NR_1$—$R_A$—$CH_2$—$CH_2$;

$R_A$ is O or $NR_2$;

each $R_A$ and $R_1$ and $R_2$ are, independently, the same or different and are H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms; alicyclic; heterocyclic; a reporter molecule; an RNA cleaving group; a group for improving the pharmacokinetic properties of an oligonucleotide; or a group for improving the pharmacodynamic properties of an oligonucleotide;

4

$B_x$ is a nucleosidic base;

n is an integer greater than 0;

Q is O, S, $CH_2$, CHF or $CF_2$;

X is H; OH; alkyl or substituted alkyl having 1 to about 10 carbon atoms; alkaryl, substituted alkaryl, aralkyl, or substituted aralkyl having 7 to about 14 carbon atoms; F; Cl; Br; CN; $CF_3$; $OCF_3$; OCN; O-alkyl; S-alkyl; N-alkyl; O-alkenyl; S-alkenyl; N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino or substituted Silyl; an RNA cleaving group; a group for improving the pharmacokinetic properties of an oligonucleotide; or a group for improving the pharmacodynamic properties of an oligonucleotide.

The compounds of the invention are prepared by coupling preselected 3'-functionalized and 4'-functionalized nucleosides and/or oligonucleotides under conditions effective to form the above-noted $L_1$—$L_2$—$L_3$—$L_4$ linkages. In certain embodiments, a 3'-C-formyl nucleoside or oligonucleotide synthon is reacted with a support-bound 5'-hydroxylamino or 5'-hydrazino nucleoside or oligonucleotide synthon. In other embodiments, a 4'-C-formyl synthon is reacted with a support-bound 3'-methylhydroxylamino or 3'-methylhydrazino synthon. In still further embodiments, linkages having structure CH=N—$R_A$—$CH_2$, $CH_2$—CH=N—$R_A$, $CH_2$—$R_A$—N=CH, or $R_A$—N=CH—$CH_2$ where $R_A$ is O or $NR_1$ are formed by coupling synthons having structures II and III:

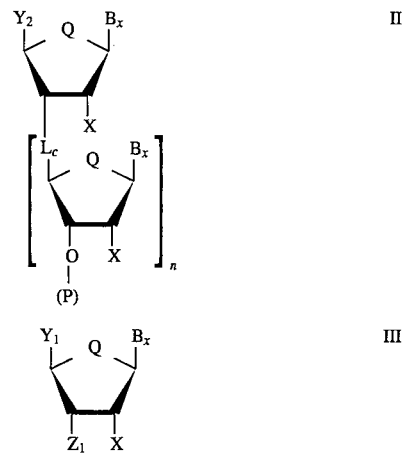

wherein:

$Z_1$ and $Y_2$ are selected such that (i) $Z_1$ is C(O)H and $Y_2$ is $CH_2CH_2R_ANH_2$;

(ii) $Z_1$ is $CH_2R_ANH_2$ and $Y_2$ is C(O)H; or (iii) $Z_1$ is $CH_2C(O)H$ and $Y_2$ is $R_ANH_2$; or (iv) $Z_1$ is $R_ANH_2$ and $Y_2$ is $H(O)CCH_2$;

$Y_1$ is OH, $OR_{HP}$, $CH_2OH$, or $CH_2OR_{HP}$ where $R_{HP}$ is a hydroxyl protecting group;

(P) is a solid support;

each $L_c$ is, independently, a covalent linkage having structure CH=N—$R_A$—$CH_2$, $CH_2$—CH=N—$R_A$, $CH_2$—RA—N=CH, $R_A$—N=CH—$CH_2$; $CH_2$—NH—$R_A$—$CH_2$, $CH_2$—$CH_2$—NH—$R_A$, $CH_2$—$R_A$—NH—$CH_2$, $R_A$—NH—$CH_2$—$CH_2$, O—$P(O)_2$O—$CH_2$, or O—P(S)(O)O—$CH_2$; and n is 0–200.

BRIEF DESCRIPTION OF THE DRAWINGS

The numerous objects and advantages of the present invention may be better understood by those skilled in the art by reference to the accompanying figures, in which:

FIGS. 1 and 2 show exemplary compounds used in accordance with the invention.

DETAILED DESCRIPTION OF THE INVENTION

Figure 3:
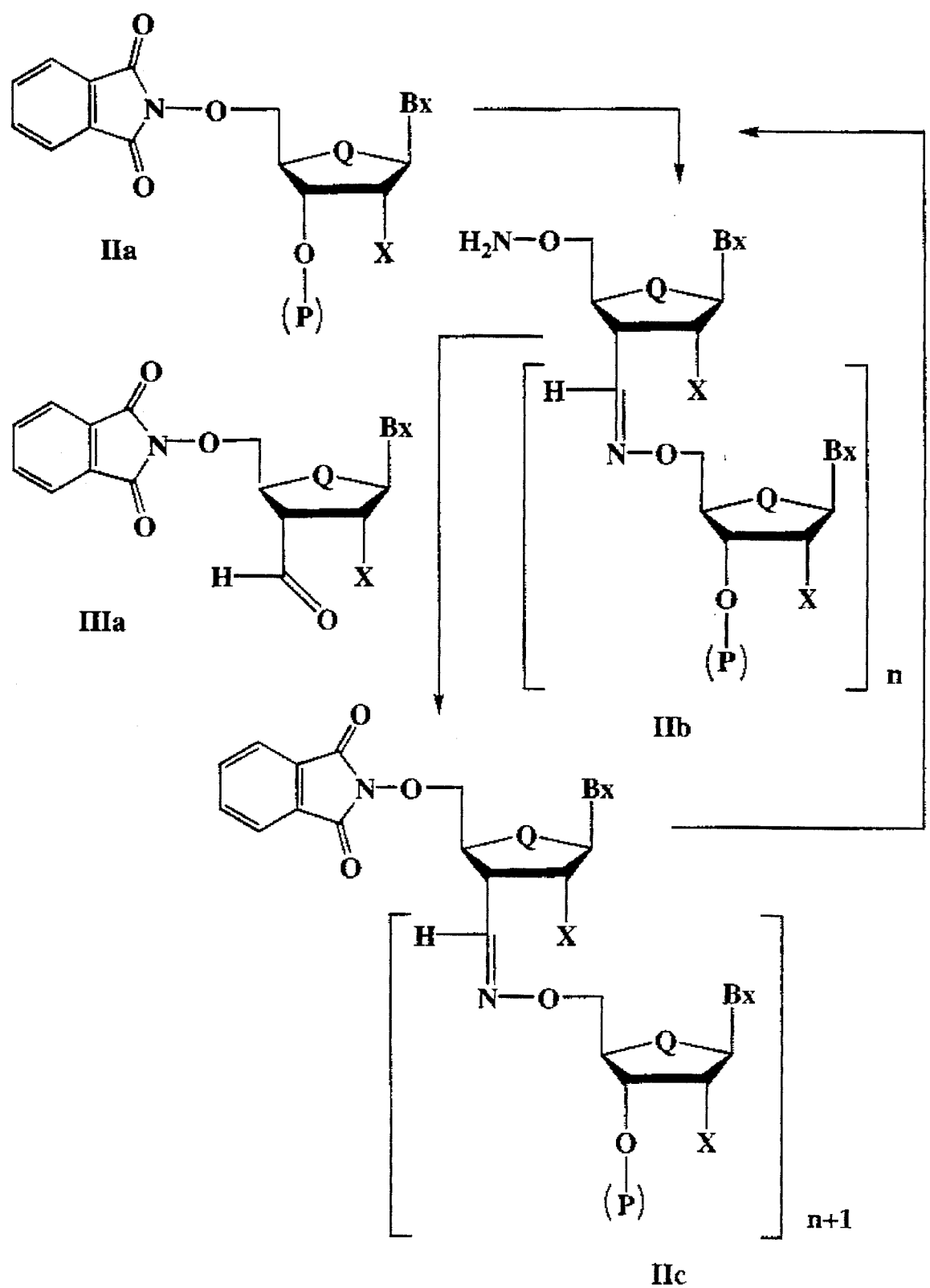
FIG. 3 is a synthetic scheme depicting a preferred method for preparation of oxime-linked oligonucleotide analogs.

The term "nucleoside" as used in connection with this invention refers to a unit made up of a heterocyclic base and its sugar. The term "nucleotide" refers to a nucleoside having a phosphate group on its 3' or 5' sugar hydroxyl group. Thus nucleosides, unlike nucleotides, have no phosphate group. "Oligonucleotide" refers to a plurality of joined nucleotide units formed in a specific sequence from naturally occurring bases and pentofuranosyl groups joined through a sugar group by native phosphodiester bonds. This term refers to both naturally occurring and synthetic species formed from naturally occurring subunits.

The compounds of the invention generally can be viewed as "oligonucleotide analogs", that is, compounds which function like oligonucleotides but which have non-naturally occurring portions. Oligonucleotide analogs can have altered sugar moieties, altered base moieties or altered inter-sugar linkages. For the purposes of this invention, an oligonucleotide analog having non-phosphodiester bonds, i.e., an altered inter-sugar linkage, is considered to be an "oligonucleoside." The term "oligonucleoside" thus refers to a plurality of nucleoside units joined by linking groups other than native phosphodiester linking groups. The term "oligomers" is intended to encompass oligonucleotides, oligonucleotide analogs or oligonucleosides. Thus, in speaking of "oligomers" reference is made to a series of nucleosides or nucleoside analogs that are joined via either natural phosphodiester bonds or other linkages, including the four atom linkers of this invention. Although the linkage generally is from the 3' carbon of one nucleoside to the 5' carbon of a second nucleoside, the term "oligomer" can also include other linkages such as 2'-5' linkages.

Oligonucleotide analogs also can include other modifications consistent with the spirit of this invention, particularly modifications that increase nuclease resistance. For example, when the sugar portion of a nucleoside or nucleotide is replaced by a carbocyclic moiety, it is no longer a sugar. Moreover, when other substitutions, such a substitution for the inter-sugar phosphorodiester linkage are made, the resulting material is no longer a true nucleic acid species. All such compounds are considered to be analogs. Throughout this specification, reference to the sugar portion of a nucleic acid species shall be understood to refer to either a true sugar or to a species taking the structural place of the sugar of wild type nucleic acids. Moreover, reference to inter-sugar linkages shall be taken to include moieties serving to join the sugar or sugar analog portions in the fashion of wild type nucleic acids.

This invention concerns modified oligonucleotides, i.e., oligonucleotide analogs or oligonucleosides, and methods for effecting the modifications. These modified oligonucleotides and oligonucleotide analogs exhibit increased chemical and/or enzymatic stability relative to their naturally occurring counterparts. Extracellular and intracellular nucleases generally do not recognize and therefore do not bind to the backbone-modified compounds of the invention. In addition, the neutral or positively charged backbones of the present invention can be taken into cells by simple passive transport rather than by complicated protein-mediated processes. Another advantage of the invention is that the lack of a negatively charged backbone facilitates sequence specific binding of the oligonucleotide analogs or oligonucleosides to targeted RNA, which has a negatively charged backbone and will repel similarly charged oligonucleotides. Still another advantage of the present invention is it presents sites for attaching functional groups that initiate cleavage of targeted RNA.

The modified internucleoside linkages of this invention are intended to replace naturally-occurring phosphodiester-5'-methylene linkages with four atom linking groups to confer nuclease resistance and enhanced cellular uptake to the resulting compound. Preferred linkages have structure $CH_2-R_A-NR_1CH_2$, $CH_2-NR_1-R_A-CH_2$, $R_A-NR_1-CH_2-CH_2$, $CH_2-CH_2-NR_1-R_A$, $CH_2-CH_2-R_A-NR_1$, or $NR_1-R_A-CH_2-CH_2$ where $R_A$ is O or $NR_2$.

Generally, these linkages are prepared by functionalizing the sugar moieties of two nucleosides which ultimately are to be adjacent to one another in the selected sequence. In a 4' to 3' sense, an "upstream" synthon such as structure III is modified at its terminal 3' site, while a "downstream" synthon such as structure II is modified at its terminal 4' site. More specifically, the invention provides efficient syntheses of oligonucleosides via intermolecular reductive coupling on a solid support.

$B_x$ can be nucleosidic bases selected from adenine, guanine, uracil, thymine, cytosine, 2-aminoadenosine or 5methylcytosine, although other non-naturally occurring species can be employed to provide stable duplex or triplex formation with, for example, DNA. Representative bases are disclosed in U.S. Pat. No. 3,687,808 (Merigan, et al.), which is incorporated herein by reference.

Q can be S, $CH_2$, CHF $CF_2$ or, preferably, O. See, e.g., Bellon, et al., *Nucleic Acids Res.* 1993, 21, 1587.

X can be H, OH, alkyl, substituted alkyl, alkaryl or aralkyl, F, Cl, Br, CN, $CF_3$, $OCF_3$, OCN, O-alkyl, S-alkyl, N-alkyl, O-alkenyl, S-alkenyl, N-alkenyl, $SOCH_3$, $SOCH_3$, $ONO_2$, $NO_2$, $N_3$, $NH_2$, heterocycloalkyl, heterocycloalkaryl, aminoalkylamino, polyalkylamino or substituted silyl, an RNA cleaving group, a group for improving the pharmacokinetic properties of an oligonucleotide, or a group for improving the pharmacodynamic properties of an oligonucleotide. It is intended that the term "alkyl" denote branched and straight chain hydrocarbyl residues, including alkyl groups having one or more $^3H$ and/or $^{14}C$ atoms. It is preferred that X is H or OH, or, alternatively F, O-alkyl or O-alkenyl, especially where Q is O. Preferred alkyl and alkenyl groups have from 1 to about 10 carbon atoms.

Solid supports (e.g., (P)) according to the invention include any of those known in the art for polynucleotide synthesis, including controlled pore glass (CPG), oxalyl-controlled pore glass (see, e.g., Alul, et al., *Nucleic Acids Research* 1991, 19, 1527), TentaGel Support—an aminopolyethyleneglycol derivatized support (see, e.g., Wright, etal., *Tetrahedron Letters* 1993, 34, 3373) or Poros—a copolymer of polystyrene/divinylbenzene. Attachment and cleavage of nucleosides and oligonucleosides can be effected via standard procedures. See, e.g., Pon, R.T. in Protocols for Oligonucleotides and Analogs, Agrawal, S., ed., Humana Press, Totowa, N.J., 1993. As used herein, the term solid support further includes any linkers (e.g., long chain alkyl amines and succinyl residues) used to bind a growing oligonucleoside to a stationary phase such as CPG.

$Y_1$ can be OH, $OR_{HP}$, $CH_2OH$, or $CH_2OR_{HP}$ where $R_{HP}$ is a hydroxyl protecting group. A wide variety of hydroxyl protecting groups can be employed in the methods of the invention. See, e.g., Beaucage, etal., *Tetrahedron* 1992, 12, 2223. In general, protecting groups render chemical functionality inert to specific reaction conditions, and can be appended to and removed from such functionality in a molecule without substantially damaging the remainder of the molecule. Representative hydroxyl protecting groups include phthalimido, t-butyldimethylsilyl (TBDMS), t-butyldiphenylsilyl (TBDPS), fluorenylmethoxycarbonyl (FMOC), and other hydroxyl protecting groups.

It is preferred that the oligonucleotide analogs of the invention comprise from about 5 to about 50 subunits having the given structure (i.e., n=5–50). While each subunit of the oligonucleotide analogs can have repetitive structure I, such need not be the case. For example, the subunits can have alternating or more random structures.

The invention is also directed to methods for the preparation of oligonucleosides with modified inter-sugar linkages. These modifications may be effected using solid supports which may be manually manipulated or used in conjunction with a DNA synthesizer using methodology commonly known to those skilled in DNA synthesizer arts. Generally, the procedure involves functionalizing the sugar moieties of two nucleosides which will be adjacent to one another in the selected sequence. In a 5' to 3' sense, an "upstream" synthon such as structure II is modified at its terminal 3' site, while a "downstream" synthon such as structure III is modified at its terminal 5' site.

More specifically, certain linkages can be formed by selecting a 3'-C-formyl derivatized compound as the upstream synthon and a 5'-aminohydroxy derivatized compound as the downstream synthon. Coupling then is effected to provide, for example, a dinucleoside having an oxime linkage. In this instance, the oxime is present as E/Z isomers. The oxime nitrogen atom is adjacent to a carbon atom on the 3' end of the upstream nucleoside. Dinucleosides having the oxime nitrogen adjacent to a carbon atom on the 5' or downstream nucleoside are synthesized utilizing a 4'-C-formyl derivatized compound as the upstream synthon and a 3'-deoxy-3'-aminohydroxymethyl derivatized compound as the downstream synthon, again providing E/Z isomers. In both instances the oxime linked compound can be incorporated directly into an oligomer and/or can be reduced to a corresponding hydroxyamino linked species. Reduction of oxime linked dinucleosides either as the dinucleoside or as a dinucleoside moiety in an oligomer with sodium cyanoborohydride yields the corresponding hydroxyamino linked compounds. Hydroxyamino linked compounds can be alkylated at the amino moiety of the hydroxyamino linkage to yield a corresponding N-alkylamino linkage.

3'-C-formyl derivatized nucleosides can be formed via several synthetic pathways. The presently preferred method utilizes a stereoselective intermolecular radical C—C bond formation reaction. (see, e.g., U.S. application Ser. No. 08/040,903, filed Mar. 31, 1993). Thus, a 3'-O-phenylthiocarbonate ester derivative of thymidine reacted with β-tri-n-butylstannylstyrene and AIBN to provide a 3'-C-styryl derivative, which on oxidative cleavage gave a 3'-C-formyl thymidine derivative. In a similar manner, a radical carbonylation of the corresponding 3'-deoxy-3'-iodo nucleoside gives the 3'-C-formyl nucleotide analog. The iodo compound is treated with CO, 2,2'-azobisisobutrylonitrile (AIBN), and tris(trimethylsilyl)silane (TTMS). Alternately, 3'-C-formyl derivatized compounds can be synthesized from either a 3'-deoxy-3'-cyano sugar or nucleoside. Both 4'-C-formyl (also identified as 5'-aldehydo) and 3'-C-formyl group can be blocked in a facile manner utilizing O-methylaminobenzenthiol as a blocking group. The 4'- and 3'-C-formyl groups can be deblocked with silver nitrate oxidation.

An alternate method of 3'-C-formyl nucleoside synthesis employs 1-O-methyl-3'-deoxy-3'-Q-methylaminobenzene thiol-5'-O-trityl-β-D-erythro-pento furanoside, which serves as a precursor for any 3'-deoxy-3'-C-formyl nucleoside. The 1-O-methyl-3'-deoxy-3'-O-methyl amino benzenethiol-5'-O-trityl-β-D-erythro-pentofuranoside is reacted with an appropriate base utilizing standard glycosylation conditions and then deblocked to yield the nucleoside. In yet another method, a 3'-deoxy-3'-cyano nucleoside is prepared from either the corresponding 3'-deoxy-3'-iodo nucleoside or by glycosylation with 1-O-methyl-3'-deoxy-3'-O-cyano-5'-O-trityl-β-D-erythro-pentofuranoside.

Oligonucleosides according to the invention, linked by hydrazines, hydroxylamines and other linking groups, can be protected by a dimethoxytrityl group at the 5'-hydroxyl and activated for coupling at the 3'-hydroxyl with cyanoethyldiisopropyl-phosphite moieties. These compounds can be inserted into any desired sequence by standard, solid phase, automated DNA synthesis techniques. One of the most popular processes is the phosphoramidite technique (see, e.g., Beaucage, et al., *Tetrahedron* 1992, 48, 2223 and references cited therein), wherein a nucleoside or oligonucleotide having a free hydroxyl group is reacted with a protected 2'-cyanoethyl phosphoramidite monomer or oligomer in the presence of a weak acid to form a phosphite-linked structure. Oxidation of the phosphite linkage followed by hydrolysis of the cyanoethyl group yields the desired phosphate or phosphorothioate linkage. In one embodiment of the invention, protected.oligonucleosides are linked with the units of a specified DNA sequence utilizing normal phosphodiester bonds. The resulting oligonucleotide analog or oligomer has a "mixed" backbone containing both phosphodiester linkages and four atom linkages of the inventions. In this manner, a sequence-specific 15-mer oligonucleotide canbe synthesized to have seven hydroxylamine, hydrazine or other type linked dinucleosides attached via alternating phosphodiester linkages. Such a structure will provide increased solubility in water compared to fully modified oligomers, which may contain linkages of the invention.

Oligonucleosides containing a uniform backbone linkage can be synthesized by use of CPG-solid support and standard nucleic acid synthesizing machines such as Applied Biosystems Inc. 380B and 394 and Milligen/Biosearch 7500 and 8800s. The initial nucleoside (number 1 at the 3'-terminus) is attached to a solid support such as controlled pore glass. In sequence specific order, each new nucleoside is attached either by manual manipulation or by the automated synthesizer system. One preferred method, shown in FIG. 1, employs a solid support to which has been bound a downstream synthon having a protected 5' site. The 5' site preferably is protected with a phthalimido group. This permits the extent of nucleoside loading on the support to be determined by UV/visible spectrophotometry, as treatment with 3% N-methylhydrazine in methylene chloride yields 1,2-dihydro-4-hydroxy-2-methyl-1-oxaphthalazine (DHMO), which has $\lambda_{max}$=304 nm and $\epsilon$=6,000 1 cm$^{-1}$ mol$^{-1}$. In addition, emission spectroscopy has been utilized to determine the percent deblocking of the 5'-O-phthalimido group by measuring the release of DHMO. (see, e.g., Example 11). The 5' site of the downstream synthon can be liberated with any nucleophilic base having a pKa from about 7.7 to about 10.0. The selected base should not appreciably react with any linker used to bind a growing oligonucleoside to a stationary phase. Representative bases include hydrazine and methylhydrazine. The 5' site preferably is liberated with 3% methylhydrazine in methylene chloride and washed with methylene chloride:methanol. The aminohydroxyl group at the 5' position of the upstream synthon also is protected with a phthalimido group to yield a 5' phthalimido protected 3'-deoxy-3'-C-formyl nucleoside, which is reacted with the downstream synthon in, for example, 2.5% acetic acid in methylene chloride. Deprotection at the 5' position and washing liberates the next 5'-aminohydroxy reaction site. The cycle is repeated with the further addition of upstream synthon until the desired sequence is constructed. Each nucleoside of this sequence is connected with oxime linkages. The terminal nucleoside of the desired oligonucleoside preferably is added to the sequence as a 5'-OTBDMS blocked 3'-deoxy-3'-C-formyl nucleoside. The oxime linked oligonucleoside can be removed from the support with, for example, ammonium hydroxide. If an aminohydroxyl linked oligonucleoside is desired, the oxime linkages are reduced with sodium cyanoborohydride in acetic acid. Alternately reduction can be accomplished while the oxime linked oligonucleoside is still attached to the support.

Free amino groups produced upon reduction can be alkylated with, for example, acetone and sodium cyanoborohydride in acetic acid. The alkylation step can be used to introduce other, useful, functional molecules on the macromolecule. Such useful functional molecules include but are not limited to reporter molecules, RNA cleaving groups, groups for improving the pharmacokinetic properties of an oligonucleotide, and groups for improving the pharmacodynamic properties of an oligonucleotide. Such molecules can be attached to or conjugated to the macromolecule via attachment to the nitrogen atom in the backbone linkage. Alternatively, such molecules can be attached to pendent groups extending from the 2' position of the sugar moiety of one or more of the nucleosides of the macromolecules. Examples of such other useful functional groups are provided by U.S. patent application Ser. No. 782,374, filed Oct. 24, 1991, now abandoned entitled Derivatized Oligonucleotides Having Improved Uptake & Other Properties, assigned to the same assignee as this application, herein incorporated by reference, and in other of the above-referenced patent applications.

The compounds of this invention can be used in diagnostics, therapeutics, and as research reagents and kits. For therapeutic use the oligonucleotide analog is administered to an animal suffering from a disease modulated by some protein. It is preferred to administer to patients suspected of suffering from such a disease an amount of oligonucleotide analog that is effective to reduce the symptomology of that disease. One skilled in the art can determine optimum dosages and treatment schedules for such treatment regimens.

It is preferred that the RNA or DNA portion which is to be modulated be preselected to comprise that portion of DNA or RNA which codes for the protein whose formation or activity is to be modulated. The targeting portion of the composition to be employed is, thus, selected to be complementary to the preselected portion of DNA or RNA, that is to be an antisense oligonucleotide for that portion.

In accordance with one preferred embodiment of this invention, the compounds of the invention hybridize to HIV mRNA encoding the tat protein, or to the TAR region of HIV mRNA. In another preferred embodiment, the compounds mimic the secondary structure of the TAR region of HIV mRNA, and by doing so bind the tat protein. Other preferred compounds complementary sequences for herpes, papilloma and other viruses.

It is generally preferred to administer the therapeutic agents in accordance with this invention internally such as orally, intravenously, or intramuscularly. Other forms of administration, such as transdermally, topically, or intralesionally may also be useful. Inclusion in suppositories may also be useful. Use of pharmacologically acceptable carriers is also preferred for some embodiments.

This invention is also directed to methods for the selective binding of RNA for research and diagnostic purposes. Such selective, strong binding is accomplished by interacting such RNA or DNA with compositions of the invention which are resistant to degradative nucleases and which hybridize more strongly and with greater fidelity than known oligonucleotides or oligonucleotide analogs.

Additional objects, advantages, and novel features of this invention will become apparent to those skilled in the art upon examination of the following examples thereof, which are not intended to be limiting, wherein parts and percents are by weight unless otherwise indicated.

EXAMPLE 1

Capping Of Free Amino Group Of Succinyl-CPG, 2

To a suspension of succinyl-CPG [1, (10.0 g), prepared according to the procedure of Damha, et al., *Nucleic Acids Res.* 1990, 18, 3813–21], in glacial acetic acid (50 ml), 20 % formaldehyde in water (1.0 ml) was added. The resulting mixture was shaken for 15 minutes. Sodium cyanoborohydride (180 mg) was added in two portions with 5 minutes shaking between each addition. Addition of 20% formaldehyde in water followed by a double reduction with sodium cyanoborohydride was repeated once. The CPG beads were washed thoroughly with dichloromethane methanol (3×50 ml, 1:1, v/v) and cloudy solution was decanted. Finally, CPG beads 2 were filtered off and washed with ethyl ether and dried under vacuum for 6 hours.

EXAMPLE 2

CPG Loading

A. 5'-O-Phthalimido-3'-O-(succinyl-CPG-NMe$_2$)thymidine, 8

5'-O-Phthalimidothymidine (3, 0.8 mmol.), dimethylaminopyridine (0.2 mmol.), 2 (2.0 g), triethylamine (160μl) and DEC (4.0 mmol.) were shaken together in dry pyridine (24 ml) for 66 hours. Pentachlorophenol (1.0 mmol) was added and the resulting mixture was shaken for 24 hours. The CPG beads were filtered off and washed thoroughly with pyridine (30 ml), dichloromethane (30 ml) and ether (30 ml). The CPG beads then were dried under vacuum for 2 hours. Then, the CPG beads were shaken with piperidine (10 ml) for 15 minutes, filtered off and washed with dichloromethane (30 ml) ether (30 ml) and dried under vacuum for 4 hours. The resulting beads were suspended in glacial acetic acid (10 ml) and sonicated for 30 minutes. The suspension was diluted with methanol dichloromethane (3×30 ml, 1:1 v/v) and cloudy solution was decanted. Then, the CPG beads were filtered off washed with dichloromethane (30 ml) and ether (30 ml) and dried under vacuum over P$_2$O$_5$ for 12 hours, to yield to 8. The loading was 35 μmol of 3 per gram of CPG.

B. 5'-O-Phthalimido-3'-O-(succinyl-CPG-NMe$_2$)-2'-deoxyadenosine, 9

The procedure of Example 2A was repeated except that 5'-O-phthalimido-2'-deoxyadenosine 4 was used in place of 5'-O-phthalimidothymidine. The loading was 36 µmol of 4 per gram of CPG.

C. 5'-O-Phthalimido-3'-O-(succinyl-CpG-NMe$_2$)-2'-isobutyryl-O -6-diphenylcarbamoyl-2'-deoxyguanosine, 10

The procedure of Example 2A was repeated except that 5'-O-phthalimido-N-2-isobutyryl-)-6-diphenylcarbamoyl-2'-deoxyguanosine 5 was used in place of 5'-O-phthalimidothymidine. The loading was 38 µmol of 5 per gram of CPG.

D. 5'-O-Phthalimido-3'-O-(succinyl-CpG-NMe$_2$)-N-4-protected-2'-deoxycytidine, 11

The procedure of Example 2A was repeated except that 5'-O-phthalimido-N-4-benzoyl-2'-deoxycytidine 6 was used in place of 5'-O-phthalimidothymidine. The loading was 32 µmol of 6 per gram of CPG.

E. 5'-O-Phthalimido-3'-O-(succinyl-CPG-NMe2)-5-methyl-N-4-protected-2'-deoxycytidine, 12

The procedure of Example 2A is repeated except that 5'-O-phthalimido-5-methyl-N-4-benzoyl-2'-deoxycytidine 7 is used in place of 5'-O-phthalimidothymidine.

EXAMPLE 3

Synthesis of Homothymidylate
3'-De(oxyphosphinico)-3'-[methylene(methylimino)] backbone, T12 MMI A. Step 1.

5'-O-Phthalimidothymidine-3'-O-succinyl-CpG (7, 28 mg, 1µmol of nucleoside) was packed into a small column and connected on an ABI DNA synthesizer model 380B. Compound 7 was treated with a solution 3% N-methyl hydrazine in dichloromethane: methanol (9:1 v/v) for 120 seconds with a 300 second wait step to give 5'-O-aminothymidine-3'-O-succinyl-CPG.

B. Step 2.

The CPG was washed with dichloromethane for 240 seconds.

C. Step 3.

5'-O-Phthalimido-3'-C-aldehydo-3'-deoxythymidine 13 in a 0.1M solution of dichloromethane mixed with a 5% glacial acetic acid in dichloromethane (1:1, v/v) was passed through the column for 15 seconds (20 eq.) with a 600 minute wait step.

D. Step 4.

The CPG was washed with dichloromethane for 150 seconds.

E. Step 5.

Steps 1–4 were repeated ten times.

F. Step 6.

The 5-terminal nucleotide, e.g., 5'-t-butyldiphenylsilyl-3'-aldehyde-3'-deoxy-thymidine 18, was incorporated following step 3. The excess of 18 was removed by washing step 4.

G. Step 7.

The resulting CPG beads (with oligomer) were transferred into a small flask and 1.0 ml of glacial acetic acid was added. NaCNBH$_3$ (15 mg) was added and the mixture was shaken and sonicated for 15 minutes. Formaldehyde (20% in water, 100µl) was added, the mixture was sonicated for 15 minutes and NaCNBH$_3$ (2×15mg) was added with 15 minutes sonication between each addition. The resulting beads were washed with methanol dichloromethane (1:1, v/v, 15 ml).

H. Step 8.

Oligomer was cleaved from the solid support by treatment with 30% ammonia for 2 hours at room temperature. The ammonia then was evaporated.

I. Step 9.

The dried residue was dissolved in tetrahydrofuran (THF)/dioxane (1.0 ml, 1:1 v/v). Tetrabutylammonium fluoride (TBAF) solution (1.0M) in THF (40µl) was added and the mixture was stirred for 16 hours. The resulting suspension was diluted with triethyl ammonium acetate (pH 7.0, 500 µl of 50 mM solution) and was concentrated under vacuum.

J. Step 10.

Purification of the oligomer of step 9 was effected by HPLC. A reverse phase Supelcosil LC-18 (5 µm, 5.0×0.46 cm) column and a precolumn (5 µm, 1.0×0.46 cm) were used for purifications. The optimal separation was achieved by elution (1 ml/minute) with ammonium acetate buffer (pH 5,9) mixed with 15% acetonitrile and increasing the polarity with 50% of acetonitrile in 25 minutes, The desired T$_{12}$ oligomer was eluted (retention time=28,8 minutes) with isocratic 1:1 acetonitrile and ammonium acetate.

EXAMPLE 4

Synthesis Of Mixed Phosphodiester And MMI
Linked Oligomer: 5'-TPT*T*T-3'
[p=3'-O-P(O)2-O-5'; *=3'CH$_2$—N (CH$_3$)—O—5']

CPG-loaded T.T oxime dimer was prepared as described in Example 3. Thus, twice repeating the steps 1–4 provided T*T oxime dimer. This dimer was further extended by repeating steps 1–4 using a 5'O-FMOC (9fluorenylmethoxycarbonyl) protected nucleoside 23 instead of nucleoside 13 during step 3. This modification provides a convenient way of switching to standard phosphoramidite chemistry without removing the CPG from automated DNA synthesizer. The resulting T*T*T oxime trimer, still attached to CPG, was treated with a solution of 5% piperidine in acetonitrile for two minutes with a flow rate of 1.6 ml/minute. A three minute waiting step and a three minute acetonitrile wash step following the piperidine treatment removed the 5'—O—FMOC group completely (see, e.g., Ma et al. *Biopolymers* 1989, 28, 965–993).

The T*T*T oxime trimer bearing a free 5'—OH group now was ready for a standard phosphoramidite cycle of DNA synthesis. Thymidine was incorporated as the last residue utilizing a procedure generally in accordance with Oligonucleotide Synthesis, M.J. Gait, ed., IRL Press, Oxford, 1984, to furnish a tetramer. The two oxime linkages of the tetramer were reduced and methylated following NaCNBH$_3$/AcOH/HCHO treatments as described in step 7 of Example 3. The resulting tetramer was cleaved from the CPG following step 8 of Example 3. The crude tetramer was purified by HPLC in a similar protocol as described in step 10 of Example 7. The title compound was eluted (retention time=26.4 minutes) over 30 minutes with an acetonitrile gradient of 5% to 25% mixed with buffer (triethylammonium acetate, pH 5.9). The product was further characterized by mass spectra (calculated 1614.57; observed 1614.25) and capillary gel electrophoresis (CE; 10% polyacrylamide, 45 cm ×75 µm capillary, 30 KV/30° C.) as clean material (single peak at 5.6 minutes retention time on CE).

EXAMPLE 5

Synthesis Of Mixed Phosphorothioate And MMI Linked Oligomer

5'-TpsT*T-3'  [ps=3'-O-P(O)(S)-O-5';  *=3'—CH$_2$—N(CH$_3$)-O-5']

T*T*T oxime trimer was prepared as described in Example 4. The last thymidine nucleoside residue was incorporate utilizing standard phosphoramidite chemistry, followed sulfurization with Beaucage reagent (see, Beaucage et al., *Tetrahedron* 1992, 48, 2223-2312) to provide a CPG attached tetramer. The CPG was taken off the DNA synthesizer and treated in a manner described in steps 7 and 8 of Example 3. The product was purified by reverse phase HPLC as described in step 10 of Example 3. The title compound was eluted (retention time=24.5 and 25.6 minutes) over 30 minutes as a mixture of diastereoisomers (due to chiral P=S) with an acetonitrile gradient of 5% to 30% mixed with buffer (triethylammonium acetate, pH 5.9). The product was further characterized by mass spectra and CE.

EXAMPLE 6

Synthesis Of Chimeric Oligomers

A. 5'-MMI Capped phosphorothioate T*T*Cme*T$_s$C$_2$G$_s$C$_s$T$_s$G$_s$G$_s$T$_s$G$_s$A$_s$G$_s$ T$_s$T$_s$T$_s$C [*=3'-CH$_2$-N(CH$_3$)-O-5'; Cme=5-methylcytosine; s=3'-O-P(O)(S)-O-5']

The 5'-O-trityl off phosphorothioate oligonucleotide (T$_s$C$_s$G$_s$C$_s$T$_s$G$_s$G$_s$T$_s$G$_s$A$_s$G$_s$T$_s$T$_s$ T$_s$C) was synthesized on a DNA synthesizer in 1µM scale on a CPG support utilizing standard phosphoramidite chemistry. (see, Zon in Protocols For Oligonucleotides and Analogs, pages 165–189, S. Agrawal, Humana Press, Totowa, N.J., 1993). Next, coupling was performed with the 5'-O-phthalimido-3'-O-phosphoramidite derivative of thymidine 28 via standard procedures to provide a protected 5'-O-amino end of the oligomer.

The 5'-O-phthalimido group was deprotected generally in accordance with the procedure of step 1 of Example 3. The CPG was then washed with dichloromethane for 240 seconds. N-4-benzoyl-3'-deoxy-3'-C-formyl-5'-O-phtalimido-5-methylcytosine 17 was then coupled with the oligomer on the support following the procedure of step 3 of Example 3. The CPG was washed with dichloromethane for 150 seconds. Oxime coupling was continued one more time following steps 1–4 of Example 3 with thymidine derivative 13. Lastly, 5'-O-tert-butyl-diphenylsilyl protected thymidine 18 was incorporate utilizing steps 3– 4 of Example 3. The resulting oligomer was cleaved from the support by treatment with ammonium hydroxide (2 hours, room temperature) and then heated at 55° C for 6 hours. The solution was concentrated and the residue dissolved in glacial acetic acid (2 ml). The oxime linkages were then reduced with NaCNBH$_3$ (15 mg) and methylated in the manner described in step 7 of Example 3.

The terminal TBDPS group was then removed by TBAF treatment as described in step 9 of Example 3. The crude, chimeric oligomer was then purified by HPLC in a manner described in step 10 of Example 3. The purified material had a retention time of 22.1 minutes. The chromatographic peak was broad due to a mixture of phosphorothioate diastereomers.

B. 3'- MMI Capped Phosphorothioate: G$_s$T$_s$T$_s$C$_s$T$_s$C$_s$G-$_s$C$_s$T$_s$G$_s$G$_s$T$_s$-G$_s$A$_s$G$_s$ T*T*T*C [s=3'-O-P (=0) (s)-O-5'; * =3'CH$_2$ N(CH$_3$)-O-5']

Synthesis of a tetrameric T*T*T*C building block with MMI internucleosidic linkages is achieved by the procedure described in Example 23 of Application PCT/US92/04294, filed May 21, 1993, utilizing solution phase stepwise coupling. This building block is protected with a 5'-O-DMT group and is attached to CPG via standard procedures (see, Pon, R. T. in Protocols for Oligonucleotides and Analogs, pages 465–496, Agrawal, S. ed., Humana Press, Totowa, N.J., 1993). Thus, 5'-O'DMT-T*T*T*C-CPG is packed into a 1 µM column and attached to a DNA synthesizer. The synthesis of the phosphorothioate portion is accomplished by standard phosphoramidite chemistry protocol as described in Example 6. The resulting chimeric oligomer with a 3'-MMI tail/cap is then purified by HPLC. Alternatively, the procedure described in Example 5 can be employed to prepare chimeric oligomers of any desired length and base composition.

C. 3'- and 5'-MMI Capped Phosphorothioate: T*T*C*T$_s$C$_s$G$_s$C$_s$T$_s$G$_s$-G$_s$T$_s$ G$_s$A$_s$G$_s$T*T*T*C [*=3'-CH$_2$-N(CH$_3$)-O-5'; s=3'-O-P (O) (S) O-5']

Synthesis of 3'- and 5'-end capped chimeric oligomers is accomplished by combination of the methods described in Examples 3 and 5. 5'-O-DMT blocked oligomer T*T*T*C is synthesized by incorporating appropriate building blocks (compounds 11, 23 and 13) following the protocol described in Example 3 (steps 1–6). The 5'-O-DMT group is removed from the CPG-attached oligomer utilizing standard acidic deprotection. Next, a phosphorothioate chain of desired length is synthesized onto the oxime tetramer. The 5'-cap of the MMI tetramer is attached following the protocol of Example 6(A) to furnish the title compound. Deprotection of oligomer from the support, reductive methylation of the oxime linkages, and purification by HPLC as in Examples 6(A) and 6(B) provides the oligomer of choice. Alternatively, appropriately protected tetramers are prepared by solution phase MMI chemistry as per Example 23 of Application PCT/US92/04294. The tetramers are then conjugated sequentially following standard phosphoramidite procedures.

EXAMPLE 7

Synthesis Of Mixed Base MMI Oligomers: T*T, A*T, Cme*T, and G*T

A general procedure for the synthesis of mixed base MMI linked oligomers has been developed to produce all sixteen pairs of possible dimers-(X*Y; X and/or Y=T, dC, dA, dG). The process consists of two steps on an automated DNA synthesizer (e.g., ABI 380 B) and two steps off the synthesizer.

A. Automated Reactions

1. Deprotection of the phthalimido group of 8–12 was carried out with a 3% solution of methyl hydrazine in dichloromethane and methanol (98:2, v/v) utilizing a 630 second step, followed by a dichloromethane wash step (180 seconds).

2. Amine-aldehyde coupling was carried out with a 0.1M solution of a bifunctional 3'-C-formyl nucleoside (e.g., compounds 13.27) in 20 molar equivalent excess dissolved in 25% acetic acid in dichloromethane using a 630 second step, followed by a dichloromethane washing step (130 second). The excess of bifunctional nucleosides 13–27 was recovered by simple concentration of the solutions.

B. Non-automated Reactions

1. The resulting oxime oligomers (attached to CPG) were reduced and reductively methylated in manner generally in accordance with step 7 of Example 3.

2. The oligomers were cleaved from the solid support (CPG) by ammonia treatment (55° C., 5 hours) and the resulting solution was concentrated in vacuo. The residue was diluted with 300 μl of water and the samples were analyzed by HPLC. A reverse phase C18 column (5 μm, 5.0×0.46 cm) and a short (1 cm) guard Column were used with a flow-rate of 1 ml/minute. Elution with 0.05M triethylammonium acetate (pH 7.0) mixed with acetonitrile (10%→30% for 20 minutes, 30% acetonitrile isocratic for 10 minutes) furnished clean products having the following retention times.

| | |
|---|---|
| Cme*T = | 12.6 minutes |
| A*T = | 15.2 minutes |
| T*T = | 15.5 minutes |
| G*T = | 12.9 minutes |
| T*A = | 11.8 minutes |
| G*A = | 07.2 minutes |

Each dimer bears a 5'-O-TBDPS group, which was left on the molecule to increase lipophilicity during HPLC analysis.

EXAMPLE 8

Synthesis Of 5'-O-Phthalimido-2'-deoxynucleoside Derivatives.

A. 5'-O-Phthalimidothymidine, 3

The 5'-O-phthalimidothymidine was prepared by the procedure described in the Example 6 of application Ser. No. 08/040,903.

B. 2'-Deoxy-5'-O-phtalimidoadenosine, 4

To a solution of deoxyadenosine (26.9 g, 100 mmol) in DMF (500 ml) were added N-hydroxyphthalimide (21.2 g, 130 mmol) and triphenylphosphine (34.1 g, 130 mmol). The solution was cooled to 0° C. and diisopropyl-azidocarboxylate (29.5 ml, 150 mmol) was then added dropwise. After addition, the solution was warmed to room temperature and stirred for two hours, DMF was removed under reduced pressure and the residual gum was triturated with ether (4×300ml). The precipitate was recrystallized from ethanol in three crops (24.66 g, 62%. m.p. 140°–142° C.). $^1$H—NMR (DMSO-d$_6$) a 2.28–2.40 (m, 1H, H2'), 2.76–2.90 (m, 1H, H2"), 4.18–4.28 (m, 1H, H4'), 4.41 (d, 5.1 Hz 2H, H5', H5") 451–461 (m, 1H, H3'), 5.54 (d, 4.0 Hz, 1H, OH3'), 6.38 (t, 6.9 Hz, 1H, H1'), 7.27 (s, 2H, NH2), 7.78–7.90 (m, 4H, ar-H), 8.12 (s, 1H, H2), 8.33 (s, 1H, H8). $^{13}$C—NMR (DMSO-d$_6$) δ 71.00 (C4'), 77.86 (C2'), 83.66 (C3'), 84.47 (C1'), 119.14 (C5'), 123.17 and 134.71 (C4", C5", C6", C7") 128.48 (C3", C8") 139.48 (CS), 149.05 (C4) 152.59 (C2), 156.03 (C5, C6), 162.98 (C2,, c9") Anal.: C$_{18}$H$_{16}$N$_6$O$_5$+½ CH$_3$OH, Calcd.: C, 53.88; H, 4.40; N, 20.38; Found: C, 53.64; H, 4.21; N, 20.22. Mass: [M+H]$^+$ 397, [A+2H]$^+$136.

C. 2'-Deoxy-O6-diphenylcarbamoyl -N2-isobutyryl-5'-O-phthalimidoguanosine,

To a solution of 2'deoxy-O6-diphenylcarbamoyl-N2-isobutyryl-guanosine (10.31 g, 19.36 mmoles) in THF (155 ml) and DMF (62 ml), triphenylphosphine (7.694 g, 29.04 mmoles) and N-hydroxyphthalimide (4.88 g) were added. Diisopropyl azodicarboxylate (6.2 ml) was added to the cooled (0° C.) solution over a period of 5 minutes. On complete addition, the solution was warmed to room temperature and stirred for 5 hours. The solvents were. evaporated under vacuum and the residue purified by silica gel column chromatography. Elution with dichloromethane/methanol (95:5, v/v) furnished the title compound (9.04 g, 69% yield). $^1$H—NMR (200 MHz, DMSO-d$_6$) є 10.64 (1,s,2-NH), 8.59 (1, s, H-8), 7.76 (4,s,phthaloyl), 7.5–7.16 (10, m, NO$_2$), 6.40 (1,t,1'-H), 5.54 (1,d,3'-OH), 4.64 (1,m, 3'-H), 4.48 (2, m, 5'-H, 5"-H), 4.21 (1, m, 4'-H), 3.33 (6, d, CH(CH$_3$)$_2$), 3.05 (1,m,2'-H), 2.68 (1,m, 2"-H).

D. N4-Benzoyl-2'-deoxy-5'-O-phthalimidocytosine, 6

TBDP-silylation of N4-benzoyl-2'-deoxy-5'-Odimethoxytritylcytosine was carried out generally in accordance with Example 7 of application Ser. No. 08/040,903 to furnish a 3'-TBDPSi protected nucleoside. The latter compound was treated with trichloroacetic acid to deprotect the dimethoxytrityl group and furnish N4-benzoyl-3'-O-tert-butyldiphenylsilyl-2'-deoxycytosine. 1H—NMR (200MHz, CDCl$_3$) є 8.67 (1,broad,NH), 8.16 (1, d, H-5), 7.9–7.15 (16,m,TBDP, Benzoyl, 6-H), 6.27 (1,t, 1'-H), 4.44 (1,m,3'-H), 4.035(1,m, 4'-H), 3.67 (1,dd,5'-H), 3.245 (1,dd,5"-H), 2.65 (1,m,2'-H), 2.25 (1,m,2"-H), 2.06 (1,broad, 5'-OH), 1.1 (9,s,tBu).

Mitsunobu reaction of N4-benzoyl-3'-O-tert-butyldiphenylsilyl-2'-deoxycytosine with N-hydroxyphthalimide following the procedure described above furnished 81% yield of the desired N4-benzoyl-3'-O-tert-butyldiphenylsilyl-2'-deoxy-5'-O-phthalimidocytosine. MP=175°–177° C. $^1$H—NMR (200 MHz, CDCl$_3$) a 8.61(2,d, NH, 5-H), 7.91–7.26 (20, m, benzoyl,TBDP, phthal, 6-H), 6.545 (1, m, 1'-H), 4.70(1,m,3'H), 4.17 (1,m, 3'H), 4.035 (1,dd, 5'-H), 3.67 (1,dd, 5"-H) 2.815 (1,m,2'-H), 1.95 (1,m, 2"-H), 1.18 (9,s,tBu).

Treatment of N4-benzoyl-3'-O-tert-butyldiphenylsilyl-2'-deoxy-5'-O-phthalimidocytosine with TBAF in THF furnished the title compound in 85% yield.

EXAMPLE 9

Synthesis Of 2',3'-Dideoxy-3'-C-formyl-5'-O-phtalimidonucleoside Derivatives.

A. 3'-Deoxy-3'-C-formyl-5'-O-phtalimidothymidine,

5'-O-tert-Butyldiphenylsilyl-3'-C-styrylthymidine was prepared according to the procedure described in Example 82 of application Ser. No. 08/040,903 and deblocked with TBAF to provide 3'-C-styrylthymidine as a white foam in 65% yield. Anal.: C$_{18}$H$_{21}$N$_2$O$_4$ Calcd.: C% 65.63; H% 6.42; N% 8.50; Found: C% 65.23; H% 6.25; N% 8.34.

Mitsunobu reaction of 3'-C-styrylthymidine with N-hydroxyphthalimide gave 97% yield of 5'-C-phtalimido-3'-C-styrylthymidine as a white solid. Anal.: C$_{26}$H$_{23}$N$_3$O$_6$ Calcd.: C% 65.95; H% 4.89; N% 8.87; Found: C% 65.69; H% 5.11; N% 8.59.

Oxidative cleavage (OsO$_4$/NaIO$_4$) of 5'-O-phthalimido-3'-C-styrylthymidine was carried out as in Example 82 of application Ser. No. 08/040,903 to furnish the title compound 13.

This procedure constitutes an alternate method for the preparation of bifunctional nucleosides such as compounds 13–17.

B 2',3'-Dideoxy-3'-C-formyl-5'-Ophthalimidoadenosine, 14

2'-Deoxyadenosine was conveniently transformed into 5'-O-tert-butyldiphenylsilyl-2',3'-dideoxy-3'-C-styryladenosine in 60% yield utilizing the radical reaction described in Example 82 of application Ser. No. 08/040,903. The 5'-O-TBDPS group of the latter compound was deblocked to provide 2',3'-dideoxy-3'-C-styryladenosine in 91% yield, mp 215°–217° C. Anal.: $C_{18}H_{19}N_5O_2 \cdot \frac{1}{4} H_2O$ Calcd.: C% 63.23; H% 5.74; N% 20.48; Found: C% 63.31; H% 5.68; N% 20.69.

2',3'-Dideoxy-3'-C-styryladenosine underwent standard Mitsunobu reaction with N-hydroxyphthalimide to provide 2',3'-dideoxy-5'-O-phthalimido-3'-C-styryladenosine in 76% yield with a melting point of 145°–147° C. Anal.: $C_{26}H_{22}N_6O_4 \cdot \frac{1}{4} H_2O$ Calcd.: C% 64.12; H% 4.65; N% 17.25; Found: C% 63.96; H% 4.58; N% 17.51.

Oxidative cleavage ($OsO_4/NaIO_4$) of the styryl group of the latter compound furnished the title compound in 55% yield as a white powder.

C. N4-Benzoyl-2',3'-dideoxy-3'-C-formyl-5'-O-phthalimido-5-methylcytosine, 17

5'-O-tert-Butyldiphenylsilyl-3'-C-styrylthymidine was converted into its 4-triazolo derivative generally according to the procedure of Li, et al., *Biochemistry* 1987, 26, 1086. The product subsequently was treated with ammonia. Benzoylation of the resulting cytosine derivative provided N4-benzoyl-5'-O-tert-butyldisphenylsilyl-2',3'-dideoxy-3'-C-styryl-5'-methylcytosine (55% yield for three steps). Deprotection of the latter product with TBAF and Mitsunobu reaction of the product furnished N4-benzoyl-2',3,-dideoxy-5'-O-phthalimido-3'-C-styryl-5-methyl-cytosine in 45% yield. Melting point=150°–155° C. Anal.: $C_{33}H_{28}N_4O_6$ Calcd.: C% 68.74; H% 4.89; N% 9.71; Found: C% 68.33; H% 4.95; N% 9.57.

This product then was treated with $OsO_4/NaIO_4$ as described in Example 82 of application Ser. No. 08/040,903 to yield title compound 17 in 57% yield as a white powder. Anal.: $C_{26}H_{22}N_4O_7 \cdot 1.25 H_2O$ Calcd.: C% 59.48; H% 4.70; N% 10.67; Found: C% 59.53; H% 4.83; N% 10.58.

D 2',3'-Dideoxy-3'-C-formyl-N2-isobutyryl 5'-O-phthalimidoguanosine, 15

2'-Deoxyguanosine was converted into the title compound 15 utilizing following reactions: (i) N2isobutyrylation generally according to R. A. Jones in Oligonucleotide Synthesis, pages 24–27, M. J. Gait, ed. IRL Press, Oxford, 1984; (ii) tert-butyldiphenylsilylation generally according to Nair, *Org. Prep. Proc. Int.* 1990, 22, 57; (iii) phenoxythiocarbonylation generally according to Robins, *J. Am. Chem. Soc.* 1983, 105, 4059; (iv) styrylation generally according to Example 82 of application Ser. No. 08/040,903; (v) desilylation by treatment with 1M TBAF in THF; (vi) Mitsunobu reaction generally according to Example 6 of application Ser. No. 08/040,903; and (vii) oxidative cleavage generally according to Example 82 of application Ser. No. 08/040,903. $^1H$ NMR ($CDCl_3$) ∈ 1.23 (m, 6, ibu H), 2.50 (m, 1, 2' H), 2.60 (m, 1, 2"H), 2.87 (m, 1, CH-ibu), 3.81 (m, 1, 5"$CH_2$), 4.1–4.4 (m, 3, 3'H, 4'H, 5"$CH_2$), 6.03 (m, 1, 1'H), 7.5–8.2 (m, 4, ArH), 8.08 (s, 1, C8H), 9.79 (s, 1, CHO), 12.24 (s, 1, NH).

EXAMPLE 10

Synthesis Of
2',3'-Dideoxy-5'-O-FMOC-3'-C-formylnucleosides

A. 3'-Deoxy-5'-O-FMOC-3'-C-formylthymidine, 23

3'-Deoxy-3'-C-styrylthymidine was protected with FMOC-Cl generally according to Balgobin, et al., Nucleosides and *Nucleotides* 1987, 6, 461, to furnish 5'-O-FMOC-3'-deoxy-3'-C-styrylthymidine in 96% yield as a yellow foam. Anal.: $C_{33}H_{30}N_2O_6 \cdot \frac{1}{2} H_2O$ Calcd.: C% 70.82; H% 5.58; N% 5.00; Found: C% 70.53; H% 5.48; N% 4.98.

Oxidative cleavage ($O_sO_4/NaIO_4$) of the former compound gave title compound 23 in 57% yield. $^1H$ NMR ($CDCl_3$) ∈ 1.80 (s, 3, $CH_3$), 2.22, 2.71 (2m, 2, 2'$CH_2$), 3.15 (m,1,3' CH), 4.22 ( t, 1, CHFMOC), 4.45 ( s, 2, $CH_2$ FMOC ), 4.55 ( m, 2, 5' $CH_2$), 4.62 (m, 1, 4'H), 6.06 (t, 1, 1'H), 7.3–7.80 (m, 9, Ar H, C6H), 8.3 (br s, 1, NH), 9.75 (s, 1, CHO).

In an analogous manner, 3'-C-styryl nucleoside derivatives of 2'-deoxycytidine, 2'-deoxyadenosine, and 2'-deoxyguanosine are transformed into 3'-C-formyl-5'-O-FMOC-derivatives of 2'-deoxycytidine 26, 2'-deoxyadenosine 24, and 2'-deoxyguanosine 25, respectively.

EXAMPLE 11

Deprotection Assay During Automated Synthesis Utilizing Emission Spectra

Equipment and Materials:

Luminescence Spectrophotometer: PERKIN ELMER LS50B Solvent: Spectrophotometer grade MeOH Reagents: (i) 1,2-dihydro-4-hydroxy-2-methyl-1-oxophthalazine (MW 176.175); (ii) N-methyl hydrazine (MW 46.07, d 0.866); (iii) N-hydroxyphthalimide (MW 163.13)

Synthesis:
1,2-Dihydro-4-hydroxy-2-methyl-1-oxophthalazine

N-Hydroxyphthalimide (10 g, 59.5 mmoles) was dissolved in anhydrous $CH_2Cl_2$ (300 ml) and N-methyl hydrazine (9.7 ml) was added to the stirred solution. The solution turned red and then yellow. When all the starting material had disappeared, the solvent was evaporated and the resulting oil was crystallized from anhydrous ethanol as fine needles.

Analysis Protocol

A. Neutral conditions

The spectrometer was turned on 0.5 hour prior to the measurement. A blank run was performed using spectrophotometer grade methanol. 1,2-Dihydro-4-hydroxy-2-methyl-1-oxophthalazine (0.234 mg) was then dissolved in methanol (100 ml) and the sample analyzed on the spectrophotometer. The excitation wavelength was chosen at 298 nm. and the corresponding emission was observed at 400 nm. The following concentrations (μMol) of 1,2-Dihydro-4-hydroxy-2-methyl-1-oxophthalazine were tested:

| Concentration | Intensity |
| --- | --- |
| 2.85 | 75 |
| 5.7 | 124 |
| 8.54 | 189 |
| 11.4 | 247 |
| 17.09 | 364 |

A linear plot was obtained using the equation:

$$\text{Emission} = [21.0 \times 10^6] \cdot [\text{Concentration (mol/L)}]$$

B. Basic conditions

The procedure of Example 11(A) was repeated except that the oxophthalazine sample was basified by addition of Nmethyl hydrazine (1% volume). Basification results in the decay of emission intensity by 25 units and moves the excitation wavelength to 485 nm.

C. Acidic conditions

The procedure of Example 11(A) was repeated except that the oxophthalazine sample was acidified with glacial acetic acid (0.1 ml). The intensities of the emission was enhanced considerably and the values are summarized below.

| Concentration | Intensity |
|---|---|
| 0.045 | 23.5 |
| 0.090 | 46.5 |
| 0.180 | 90.5 |
| 0.226 | 110.5 |
| 0.316 | 151 |
| 0.451 | 218.6 |
| 0.632 | 303.5 |
| 0.903 | 411 |

A graphical representation of this data provided a linear plot using the following equation:

$$\text{Intensity} = [459 \times 10^6] \cdot [\text{Concentration (mol/L)}]$$

As can be seen, sensitivity of detection was enhanced dramatically under acidic conditions. The foregoing method is very effective for the determination of low concentrations of 1,2-Dihydro-4-hydroxy-2-methyl-1-oxophthalazine during automated synthesis.

EVALUATION

PROCEDURE I—Nuclease Resistance

A. Evaluation of the resistance of oligonucleotide-mimicking macromolecules to serum and cytoplasmic nucleases.

Oligonucleotide-mimicking macromolecules of the invention can be assessed for their resistance to serum nucleases by incubation of the oligonucleotide-mimicking macromolecules in media containing various concentrations of fetal calf serum or adult human serum. Labelled oligonucleotide-mimicking macromolecules are incubated for various times, treated with protease K and then analyzed by gel electrophoresis on 20% polyacrylamine-urea denaturing gels and subsequent autoradiography. Autoradiograms are quantitated by laser densitometry. Based upon the location of the modified linkage and the known length of the oligonucleotide-mimicking macromolecules it is possible to determine the effect on nuclease degradation by the particular modification. For the cytoplasmic nucleases, an HL 60 cell line can be used. A post-mitochondrial supernatant is prepared by differential centrifugation and the labelled macromolecules are incubated in this supernatant for various times. Following the incubation, macromolecules are assessed for degradation as outlined above for serum nucleolytic degradation. Autoradiography results are quantitated for evaluation of the macromolecules of the invention. It is expected that the macromolecules will be completely resistant to serum and cytoplasmic nucleases.

B. Evaluation of the resistance of oligonucleotide-mimicking macromolecules to specific endo- and exo-nucleases.

Evaluation of the resistance of natural oligonucleotides and oligonucleotide-mimicking macromolecules of the invention to specific nucleases (i.e., endonucleases, 3',5'-exo-, and 5',3'-exonucleases) can be done to determine the exact effect of the macromolecule linkage on degradation. The oligonucleotide-mimicking macromolecules are incubated in defined reaction buffers specific for various selected nucleases. Following treatment of the products with protease K, urea is added and analysis on 20% polyacrylamide gels containing urea is done. Gel products are visualized by staining with Stains All reagent (Sigma Chemical Co.). Laser densitometry is used to quantitate the extent of degradation. The effects of the macromolecules linkage are determined for specific nucleases and compared with the results obtained from the serum and cytoplasmic systems. As with the serum and cytoplasmic nucleases, it is expected that the oligonucleotide-mimicking macromolecules of the invention will be completely resistant to endo- and exo-nucleases.

PROCEDURE 2

5-Lipoxygenase Analysis and Assays

A. Therapeutics

For therapeutic use, an animal suspected of having a disease characterized by excessive or abnormal supply of 5-lipoxygenase is treated by administering the macromolecule of the invention. Persons of ordinary skill can easily determine optimum dosages, dosing methodologies and repetition rates. Such treatment is generally continued until either a cure is effected or a diminution in the diseased state is achieved. Long term treatment is likely for some diseases.

B. Research Reagents

The oligonucleotide-mimicking macromolecules of this invention will also be useful as research reagents when used to cleave or otherwise modulate 5–lipoxygenase mRNA in crude cell lysates or in partially purified or wholly purified RNA preparations. This application of the invention is accomplished, for example, by lysing cells by standard methods, optimally extracting the RNA and then treating it with a composition at concentrations ranging, for instance, from about 100 to about 500 ng per 10 Mg of total RNA in a buffer consisting, for example, of 50 mm phosphate, pH ranging from about 4–10 at a temperature from about 30° to about 50° C. The cleaved 5–lipoxygenase RNA can be analyzed by agarose gel electrophoresis and hybridization with radiolabeled DNA probes or by other standard methods.

C. Diagnostics

The oligonucleotide-mimicking macromolecules of the invention will also be useful in diagnostic applications, particularly for the determination of the expression of specific mRNA species in various tissues or the expression of abnormal or mutant RNA species. In this example, while the macromolecules target a abnormal mRNA by being designed complementary to the abnormal sequence, they would not hybridize to normal mRNA.

Tissue samples can be homogenized, and RNA extracted by standard methods. The crude homogenate or extract can be treated for example to effect cleavage of the target RNA. The product can then be hybridized to a solid support which contains a bound oligonucleotide complementary to a region on the 5' side of the cleavage site. Both the normal and abnormal 5' region of the mRNA would bind to the solid support. The 3' region of the abnormal RNA, which is cleaved, would not be bound to the support and therefore would be separated from the normal mRNA.

Targeted mRNA species for modulation relates to 5-lipoxygenase; however, persons of ordinary skill in the art will appreciate that the present invention is not so limited and it is generally applicable. The inhibition or modulation of production of the enzyme 5-lipoxygenase is expected to have significant therapeutic benefits in the treatment of disease. In order to assess the effectiveness of the compositions, an assay or series of assays is required.

D. in Vitro Assays

The cellular assays for 5-lipoxygenase preferably use the human promyelocytic leukemia cell line HL-60. These cells can be induced to differentiate into either a monocyte like cell or neutrophil like cell by various known agents. Treatment of the cells with 1.3% dimethyl sulfoxide, DMSO, is known to promote differentiation of the cells into neutrophils. It has now been found that basal HL-60 cells do not synthesize detectable levels of 5–lipoxygenase protein or secrete leukotrienes (a downstream product of 5-lipoxygenase). Differentiation of the cells with DMSO causes an appearance of 5-lipoxygenase protein and leukotriene biosynthesis 48 hours after addition of DMSO. Thus induction of 5-lipoxygenase protein synthesis can be utilized as a test system for analysis of oligonucleotide-mimicking macromolecules which interfere with 5-lipoxygenase synthesis in these cells.

A second test system for oligonucleotide-mimicking macromolecules makes use of the fact that 5-lipoxygenase is a "suicide" enzyme in that it inactivates itself upon reacting with substrate. Treatment of differentiated HL-60 or other ISIS-0716 - 36 - PATENT cells expressing 5 lipoxygenase, with 10 μM A23187, a calcium ionophore, promotes translocation of 5-lipoxygenase from the cytosol to the membrane with subsequent activation of the enzyme. Following activation and several rounds of catalysis, the enzyme becomes catalytically inactive. Thus, treatment of the cells with calcium ionophore inactivates endogenous 5-lipoxygenase. It takes the cells approximately 24 hours to recover from A23187 treatment as measured by their ability to synthesize leukotriene $B_4$. Macromolecules directed against 5-lipoxygenase can be tested for activity in two HL-60 model systems using the following quantitative assays. The assays are described from the most direct measurement of inhibition of 5-lipoxygenase protein synthesis in intact cells to more downstream events such as measurement of 5-lipoxygenase activity in intact cells.

A direct effect which oligonucleotide-mimicking macromolecules can exert on intact cells and which can be easily be quantitated is specific inhibition of 5-lipoxygenase protein synthesis. To perform this technique, cells can be labelled with $^{35}S$-methionine (50 μCi/mL) for 2 hours at 37° C. to label newly synthesized protein. Cells are extracted to solubilize total cellular proteins and 5lipoxygenase is immunoprecipitated with 5-lipoxygenase antibody followed by elution from protein A Sepharose beads. The immunoprecipitated proteins are resolved by SDS-polyacrylamide gel electrophoresis and exposed for autoradiography. The amount of immunoprecipitated 5-lipoxygenase is quantitated by scanning densitometry.

A predicted result from these experiments would be as follows. The amount of 5-lipoxygenase protein immunoprecipitated from control cells would be normalized to 100%. Treatment of the cells with 1 μM, 10 μM, and 30 μM of the macromolecules of the invention for 48 hours would reduce immunoprecipitated 5-lipoxygenase by 5%, 25% and 75% of control, respectively.

Measurement of 5-lipoxygenase enzyme activity in cellular homogenates could also be used to quantitate the amount of enzyme present which is capable of synthesizing leukotrienes. A radiometric assay has now been developed for quantitating 5-lipoxygenase enzyme activity in cell homogenates using reverse phase HPLC. Cells are broken by sonication in a buffer containing protease inhibitors and EDTA. The cell homogenate is centrifuged at 10,000×g for 30 min and the supernatants analyzed for 5-lipoxygenase activity. Cytosolic proteins are incubated with 10 μM arachidonic acid, 2mM ATP, 50 μM free calcium, 100 μg/ml phosphatidylcholine, and 50 mM bis-Tris buffer, pH 7.0, for 5 min at 37° C. The reactions are quenched by the addition of an equal volume of acetone and the fatty acids extracted with ethyl acetate. The substrate and reaction products are separated by reverse phase HPLC on a Novapak C18 column (Waters Inc., Millford, Mass.). Radioactive peaks are detected by a Beckman model 171 radiochromatography detector. The amount of arachidonic acid converted into di-HETE's and monoHETE's is used as a measure of 5-lipoxygenase activity.

A predicted result for treatment of DMSO differentiated HL-60 cells for 72 hours with effective the macromolecules of the invention at 1 μM, 10 μM, and 30 μM would be as follows. Control cells oxidize 200 pmol arachidonic acid/5 min/. 106 cells. Cells treated with 1 μM, 10 μM, and 30 μM of an effective oligonucleotide-mimicking macromolecule would oxidize 195 pmol, 140 pmol, and 60 pmol of arachidonic acid/5 min/$10^6$ cells respectively.

A quantitative competitive enzyme linked immunosorbant assay (ELISA) for the measurement of total 5-lipoxygenase protein in cells has been developed. Human 5-lipoxygenase expressed in *E. coli* and purified by extraction, Q-Sepharose, hydroxyapatite, and reverse phase HPLC is used as a standard and as the primary antigen to coat microtiter plates. 25 ng of purified 5-lipoxygenase is bound to the microtiter plates overnight at 4° C. The wells are blocked for 90 min with 5% goat serum diluted in 20 mM Tris.HCL buffer, pH 7.4, in the presence of 150 mM NaCl (TBS). Cell extracts (0.2% Triton X-100, 12,000×g for 30 min.) or purified 5-lipoxygenase were incubated with a 1:4000 dilution of 5-lipoxygenase polyclonal antibody in a total volume of 100 μL in the microtiter wells for 90 min. The antibodies are prepared by immunizing rabbits with purified human recombinant 5-lipoxygenase. The wells are washed with TBS containing 0.05% tween 20 (TBST), then incubated with 100 μL of a 1:1000 dilution of peroxidase conjugated goat antirabbit IgG (Cappel Laboratories, Malvern, Pa.) for 60 min at 25° C. The wells are washed with TBST and the amount of peroxidase labelled second antibody determined by development with tetramethylbenzidine.

Predicted results from such an assay using a 30 mer oligonucleotide-mimicking macromolecule at 1 μM, 10 μM, and 30 μM would be 30 ng, 18 ng and 5 ng of 5-lipoxygenase per $10^s$ cells, respectively with untreated cells containing about 34 ng 5-lipoxygenase.

A net effect of inhibition of 5-lipoxygenase biosynthesis is a diminution in the quantities of leukotrienes released from stimulated cells. DMSO-differentiated HL-60 cells release leukotriene B4 upon stimulation with the calcium ionophore A23187. Leukotriene B4 released into the cell medium can be quantitated by radioimmunoassay using commercially available diagnostic kits (New England Nuclear, Boston, MA). Leukotriene B4 production can be detected in HL-60 cells 48 hours following addition of DMSO to differentiate the Cells into a neutrophil-like cell. Cells ($2 \times 10^5$ cells/mL) will be treated with increasing concentrations of the macromolecule for 48–72 hours in the presence of 1.3% DMSO. The cells are washed and resuspended at a concentration of $2 \times 10^6$ cell/mL in Dulbecco's phosphate buffered saline containing 1% delipidated bovine serum albumin. Cells are stimulated with 10 μM calcium ionophore A23187 for 15 min and the quantity of LTB4 produced from 5 x 10⁵ cell determined by radioimmunoassay as described by the manufacturer.

Using this assay the following results would likely be obtained with an oligonucleotide-mimicking macromolecule directed to the 5-LO mRNA. Cells will be treated for 72 hours with either 1 µM, 10 µM or 30 µM of the macromolecule in the presence of 1.3% DMSO. The quantity of $LTB_4$ produced from 5×10⁵ cells would be expected to be about 75 pg, 50 pg, and 35 pg, respectively with untreated differentiated cells producing 75 pg $LTB_4$.

E. In Vivo Assay

Inhibition of the production of 5-lipoxygenase in the mouse can be demonstrated in accordance with the following protocol. Topical application of arachidonic acid results in the rapid production of leukotriene B4, leukotriene $C_4$ and prostaglandin $E_2$ in the skin followed by edema and cellular infiltration. Certain inhibitors of 5-lipoxygenase have been known to exhibit activity in this assay. For the assay, 2 mg of arachidonic acid is applied to a mouse ear with the contralateral ear serving as a control. The polymorphonuclear cell infiltrate is assayed by myeloperoxidase activity in homogenates taken from a biopsy 1 hour following the administration of arachidonic acid. The edematous response is quantitated by measurement of ear thickness and wet weight of a punch biopsy. Measurement of leukotriene $B_4$ produced in biopsy specimens is performed as a direct measurement of 5-lipoxygenase activity in the tissue. Oligonucleotide-mimicking macromolecules will be applied topically to both ears 12 to 24 hours prior to administration of arachidonic acid to allow optimal activity of the compounds. Both ears are pretreated for 24 hours with either 0.1 µmol, 0.3 µmol, or 1.0 µmol of the macromolecule prior to challenge with arachidonic acid. Values are expressed as the mean for three animals per concentration. Inhibition of polymorphonuclear cell infiltration for 0.1 µmol, 0.3 µmol, and 1 µmol is expected to be about 10%, 75% and 92% of control activity, respectively. Inhibition of edema is expected to be about 3%, 58% and 90%, respectively while inhibition of leukotriene $B_4$ production would be expected to be about 15%, 79% and 99%, respectively.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A process for forming covalent linkages, comprising the steps of:

(a) providing a support-bound synthon having structure:

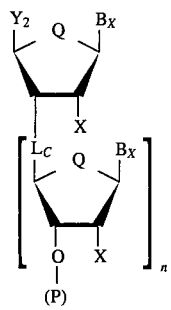

and (b) contacting said support-bound synthon with a solution-phase synthon having structure:

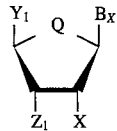

said contacting being for a time and under reaction conditions effective to form a covalent linkage having structure $CH=N-R_A-CH_2$, $CH_2-CH=N-R_A$, $CH_2-R_A-N=CH$, or $R_A-N=CH-CH_2$;

wherein:

$Z_1$ and $Y_2$ are selected such that (i) $Z_1$ is C(O)H and $Y_2$ is $CH_2R_ANH_2$; or (ii) $Z_1$ is $CH_2R_ANH_2$ and $Y_2$ is C(O)H; or (iii) $Z_1$ is $CH_2C(O)H$ and $Y_2$ is $R_ANH_2$; or (iv) $Z_1$ is $R_ANH_2$ and $Y_2$ is $CH_2C(O)H$;

each $R_A$ is, independently, O or $NR_2$;

$Y_1$ is OH, $OR_{HP}$, $CH_2OH$, or $CH_2OR_{HP}$ where $R_{HP}$ is a hydroxyl protecting group;

(P) is a solid support;

each $L_c$ is, independently, a covalent linkage having the structure $CH=N-R_A-CH_2$, $CH_2-CH=N-R_A$, $CH_2-R_A-N=CH$, $R_A-N=CH-CH_2$, $O-P(O)_2O-CH_2$, or $O-P(S)(O)O-CH_2$;

n is 0–200;

each $R_2$ is, independently, H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms;

each $B_x$ is, independently, a nucleosidic base; each Q is, independently, O or S;

and each X is, independently, H; OH; alkyl or substituted alkyl having 1 to about 10 carbon atoms; F; Cl; Br; CN; $CF_3$; $OCF_3$; OCN; O—alkyl; S—alkyl; or N—alkyl.

2. The process of claim 1 wherein $R_A$ is O.

3. The process of claim 1 wherein $R_A$ is NH or $NCH_3$.

4. The process of claim 1 wherein $Z_1$ is C(O)H and $Y_2$ is $CH_2R_ANH_2$.

5. The process of claim 1 wherein $Z_1$ is $CH_2R_ANH_2$ and $Y_2$ is C(O)H.

6. The process of claim 1 wherein $Z_1$ is $CH_2C(O)H$ and $Y_2$ is $R_ANH_2$.

7. The process of claim 1 wherein $Z_1$ is $R_ANH_2$ and $Y_2$ is $CH_2C(O)H$.

8. The process of claim 1 wherein said support bound synthon is prepared by contacting a synthon having structure:

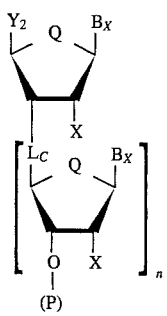

wherein $Y_2$ is $CH_2R_A$-(phthalimido) or $R_A$-(phthalimido) with hydrazine, methylhydrazine, or a combination thereof.

9. The process of claim 1 further comprising reducing said covalent linkage to form a reduced linkage having structure $CH_2$—$NR_1$—$R_A$—$CH_2$, $CH_2$—$CH_2$—$NR_1$—$R_A$, $CH_2$—$R_A$—$NR_1$—$CH_2$, or $R_A$—$NR_1$—$CH_2$—$CH_2$ wherein each $R_1$ is, independently, H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms.

10. The process of claim 9 wherein $Z_1$ is C(O)H and $Y_2$ is $CH_2R_ANH_2$.

11. The process of claim 9 wherein $R_A$ is O.

12. The process of claim 9 wherein $Z_1$ is $CH_2C(O)H$ and $Y_2$ is $R_ANH_2$.

13. The process of claim 9 further comprising alkylating a free amine group in said reduced linkage.

14. The process of claim 13 further comprising cleaving the product of said claim from said support.

15. The process of claim 1 further comprising cleaving the product of said claim from said support.

16. The process of claim 14 further comprising removing said hydroxyl protecting group from the product of said claim.

17. The process of claim 16 further comprising contacting said product in the presence of acid with a 2'-cyanoethylphosphoramidite nucleotide or a 2'-terminal cyanoethylphosphoramidite oligonucleotide to form a phosphite-linked structure.

18. The process of claim 17 further comprising oxidizing said phosphite linkage structure and hydrolyzing said cyanoethyl group.

19. The process of claim 1 further comprising removing said hydroxyl protecting group from the product of said claim.

20. A compound having structure:

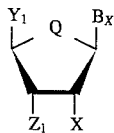

wherein:

$Z_1$ is C(O)H, $CH_2C(O)H$, $CH_2R_AN_2$, or $R_ANH_2$;

$R_A$ is O or $NR_2$;

$Y_1$ is OH, $OR_{HP}$, $CH_2OH$, or $CH_2OR_{HP}$ where $R_{HP}$ is a hydroxyl protecting group;

$R_2$ is H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms;

$B_x$ is a nucleosidic base;

Q is O, S, and

X is H; OH; alkyl or substituted alkyl having 1 to about 10 carbon atoms; F; Cl; Br; CN; $CF_3$; $OCF_3$; OCN; O-alkyl; S-alkyl; or N-alkyl.

21. The compound of claim 20 wherein $R_A$ is O.

22. The compound of claim 20 wherein $R_A$ is NH.

23. The compound of claim 20 wherein $Z_1$ is C(O)H or $CH_2C(O)H$.

24. The compound of claim 20 wherein $Z_1$ is $CH_2R_ANH_2$ or $R_ANH_2$.

25. The compound of claim 20 wherein $R_{HP}$ is phthalimido, fluorenylmethoxycarbonyl, t-butyldimethylsilyl, or t-butyldiphenylsilyl.

26. A compound having structure:

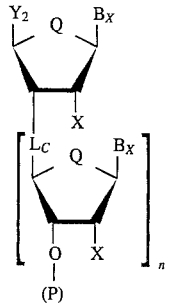

wherein:

$Y_2$ is C(O)H, $CH_2C(O)H$, $CH_2R_ANH_2$, or $R_ANH_2$;

$Z_2$ is OH, $OR_{HP}$, $CH_2OH$, or $CH_2OR_{HP}$;

n is 0–200;

(P) is a solid support;

each $L_c$ is, independently, a covalent linkage having structure CH=N—$R_A$—$CF_2$, $CH_2$—CH=N—$R_A$, $CH_2$—$R_A$—N—CH, $R_A$—N—CH—$CH_2$, $CH_2$—$NR_1$— $R_A$—$CH_2$, $CH_2$—$CH_2$—$NR_1$—$R_A$, $CH_2$—$R_A$—$NR_1$—$CH_2$, $R_A$—$NR_1$—$CH_2$—$CH_2$, O—P(O)$_2$O-$CH_2$, or O—P(S) (O)O—$CH_2$;

each $R_A$ is, independently, O or $NR_2$;

each $R_2$ and $R_2$ is, independently, H; alkyl or substituted alkyl having 1 to about 10 carbon atoms; alkenyl or substituted alkenyl having 2 to about 10 carbon atoms; alkynyl or substituted alkynyl having 2 to about 10 carbon atoms; alkaryl, substituted alkaryl, aralkyl, or substituted aralkyl having 7 to about 14 carbon atoms;

each $B_x$ is, independently, a nucleosidic base;

each Q is, independently, O or S;

and each X is, independently, H; OH; alkyl or substituted alkyl having 1 to about 10 carbon atoms.

27. The compound of claim 26 wherein $R_A$ is O.

28. The compound of claim 26 wherein $Y_2$ is $CH_2R_ANH_2$ or $R_ANH_2$.

29. The compound of claim 26 wherein $L_c$ is CH=N—$R_A$—$CH_2$, $CH_2$—CH=N—$R_A$, $CH_2$—$R_A$—N=CH, or $R_A$—N=CH—$CH_2$.

30. The compound of claim 26 wherein $L_c$ is $CH_2$—$NR_1$— $R_A$—$CH_2$, $CH_2$—$CH_2$—$NR_1$—$R_A$, $CH_2$—$R_A$—$NR_1$—CH—, or $R_A$—$NR_1$—$CH_2$—$CH_2$.

31. The compound of claim 30 wherein $R_1$ is H.

32. The compound of claim 30 wherein $R_1$ is $CH_3$.

* * * * *

UNITED STATES PATENT AND TRADEMARK OFFICE
CERTIFICATE OF CORRECTION

PATENT NO. : 5,541,307
DATED : July 30, 1996
INVENTOR(S) : Phillip D. Cook et al It is certified that error appears in the above-identified patent and that said Letters Patent is hereby corrected as shown below:

Col. 1, line 34, "hydroxylaminoc-ontaining" should be hyphenated as follows: --hydroxylamino-containing--.

Col. 15, line 55, "(C2, c9")should be -- (C2,"C9")--.

Col. 16, line 50, "5'-C-phtalimido" should be --5'-O-phtalimido-- line 62, "Ophthalimidoadenosine" should be --O-phthalimidoadenosine--.

Col. 19, line 23 "[459x106]" should be --$459 \times 10^6$ --.

Col. 21, line 64, "quantirate" should be --quantitate--.

Col. 22, line 50, "$10^s$" should be --$10^6$ --.

Col. 26, line 63, claim 30 -CH- should be --$CH_2$ --.

Signed and Sealed this

Twenty-second Day of December, 1998

Attest:

BRUCE LEHMAN

Attesting Officer

Commissioner of Patents and Trademarks